United States Patent
Schwalm et al.

(10) Patent No.: US 9,738,597 B2
(45) Date of Patent: Aug. 22, 2017

(54) METHOD FOR PREPARING URETHANE (METH)ACRYLATES

(71) Applicant: BASF SE, Ludwigshafen (DE)

(72) Inventors: Reinhold Schwalm, Wachenheim (DE); Susanne Neumann, Speyer (DE); Delphine Kimpel, Speyer (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/892,027

(22) PCT Filed: May 16, 2014

(86) PCT No.: PCT/EP2014/060059
§ 371 (c)(1),
(2) Date: Nov. 18, 2015

(87) PCT Pub. No.: WO2014/191228
PCT Pub. Date: Dec. 4, 2014

(65) Prior Publication Data
US 2016/0107987 A1    Apr. 21, 2016

(30) Foreign Application Priority Data
May 27, 2013 (EP) .................................... 13169357

(51) Int. Cl.
C07C 261/00 (2006.01)
C07C 269/00 (2006.01)
C07C 271/00 (2006.01)
C07C 269/02 (2006.01)
C08G 18/67 (2006.01)
C08G 18/68 (2006.01)
C08G 18/22 (2006.01)
C09D 175/16 (2006.01)
C07C 271/12 (2006.01)
C09D 4/00 (2006.01)

(52) U.S. Cl.
CPC .......... *C07C 269/02* (2013.01); *C07C 271/12* (2013.01); *C08G 18/222* (2013.01); *C08G 18/227* (2013.01); *C08G 18/672* (2013.01); *C08G 18/6725* (2013.01); *C08G 18/68* (2013.01); *C09D 4/00* (2013.01); *C09D 175/16* (2013.01)

(58) Field of Classification Search
CPC ... C07C 269/02; C07C 271/12; C08G 18/222; C08G 18/227; C08G 18/672; C08G 18/6725; C08G 18/68; C09D 175/16; C09D 4/00; A61G 5/10
See application file for complete search history.

(56) References Cited

U.S. PATENT DOCUMENTS

| | | | |
|---|---|---|---|
| 4,188,472 A * | 2/1980 | Chang ................ | C08G 18/4269 522/90 |
| 6,534,128 B1 | 3/2003 | Carlson et al. | |
| 7,022,778 B2 | 4/2006 | Bremer et al. | |
| 8,865,832 B2 | 10/2014 | Sommer et al. | |
| 2004/0157995 A1* | 8/2004 | Bremer ............... | C08G 18/0823 525/123 |
| 2008/0071037 A1* | 3/2008 | Carr .................... | C08G 18/4277 525/415 |
| 2011/0039971 A1 | 2/2011 | Eisele et al. | |

FOREIGN PATENT DOCUMENTS

| | | |
|---|---|---|
| DE | 2939584 | 4/1980 |
| EP | 2316867 | 5/2011 |
| WO | WO-2004/029121 | 4/2004 |

OTHER PUBLICATIONS

PCT International Search Report in PCT/EP2014/060059, mailed Oct. 8, 2014, 2 pages.

* cited by examiner

*Primary Examiner* — Yevegeny Valenrod
*Assistant Examiner* — Blaine G Doletski
(74) *Attorney, Agent, or Firm* — Marshall, Gerstein & Borun LLP

(57) ABSTRACT

Described herein is a process for preparing urethane (meth) acrylates. In a first step, a hydroxyalkyl (meth)acrylate is reacted with a lactone (B) in the presence of at least one zinc compound and/or bismuth compound (C) to produce a resulting zinc-containing product and/or a bismuth-containing product, and, in a further step, the zinc-containing product and/or the bismuth-containing product is reacted with at least one cycloaliphatic or asymmetric aliphatic diisocyanate (D).

16 Claims, No Drawings

METHOD FOR PREPARING URETHANE (METH)ACRYLATES

CROSS-REFERENCE TO RELATED APPLICATIONS

This is application is the National Stage Entry of PCT/EP2014/060059, filed May 16, 2014, which claims priority to European Patent Application No. 13169357.4, filed May 27, 2013, the disclosures of which are incorporated herein by reference in their entireties.

TECHNICAL FIELD

The present invention describes a new process for preparing urethane (meth)acrylates.

BACKGROUND

Urethane acrylates based on caprolactone-modified resins are known from U.S. Pat. No. 4,188,472, for example. In DE 2939584 (=U.S. Pat. No. 4,188,472), 2-hydroxyethyl acrylate is reacted ring-openingly with epsilon-caprolactone in the presence of various catalysts based on titanium or tin or on organic acids (sulfuric acid, p-toluenesulfonic acid), and the resulting product is subsequently reacted with diisocyanates to form the urethane.

U.S. Pat. No. 7,022,778 discloses reacting 2-hydroxyethyl acrylate with epsilon-caprolactone in the presence of zinc octoate. The product of the reaction is used as a reactive diluent in two-component polyurethane coating materials.

A disadvantage of these reaction regimes is that the catalysts disclosed result in nonuniform distribution of the addition product.

The organotin catalysts used result in a particular molecular weight distribution on reaction of hydroxyalkyl acrylates with caprolactone. In the course of this reaction, unreacted hydroxyalkyl acrylate is left, and reaction products of hydroxyalkyl acrylates with up to 10 caprolactone units are formed. However, since products with 3 or more caprolactone units show a tendency toward crystallization, their concentration ought not to be too high. Furthermore, the reaction products of the unreacted hydroxyalkyl acrylates with diisocyanates give rise to urethane acrylates of low flexibility.

In order to conform to this requirement, the viscosity of the first stage, i.e., in the reaction of hydroxyethyl acrylate with 2 mol of caprolactone, ought to be situated within a viscosity range of 60-90 mPas (measured using an Epprecht cone/plate viscometer (Cone B) at 23° C.

US 2011/039971 A1 discloses reacting a commercially available addition product of epsilon-caprolactone with 2-hydroxyethyl acrylate with further components onto trifunctional polyisocyanates to form the urethane.

Catalysts referred to for the formation of the urethane include, in general form, dibutyltin laurate, bismuth carboxylate, or zirconium chelates. The matter of which catalyst is explicitly used in the examples remains open.

U.S. Pat. No. 6,534,128 discloses reacting a commercially available addition product of epsilon-caprolactone and 2-hydroxyethyl acrylate with further components with diisocyanates to form the urethane.

Catalysts referred to for the formation of the urethane include, in general form, dibutyltin dilaurate, other organotin compounds, and organobismuth and organozirconium compounds. The examples use exclusively dibutyltin dilaurate as catalyst.

A disadvantage of these reaction regimes is that the commercially available product still contains traces of the catalyst from the preparation of the addition product, and then further catalyst is added to the reaction for the formation of the urethane as well.

SUMMARY

A first aspect of the present invention is directed to a process for preparing urethane (meth)acrylates of the formula (I)

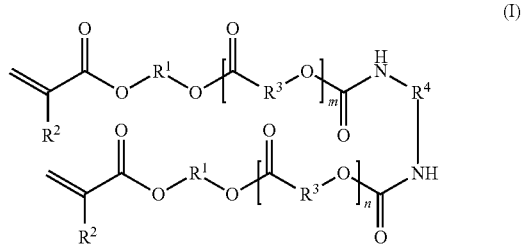

comprising, in a first step, reacting a hydroxyalkyl (meth)acrylate (A) of the formula (A)

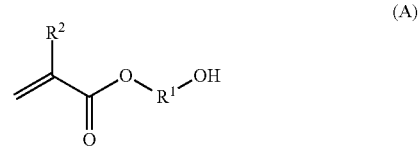

with a lactone (B) of the formula (B)

in the presence of at least one zinc compound and/or bismuth compound (C) to produce a bismuth-containing product, and, in a further step, reacting the resultant bismuth-containing product from the first step with at least one cycloaliphatic or asymmetric aliphatic diisocyanate (D), wherein $R^1$ is a divalent alkylene radical which has having 2 to 12 carbon atoms and which may optionally be substituted by $C_1$ to $C_4$ alkyl groups and/or interrupted by one or more oxygen atoms, $R^2$ in each case independently of any other is methyl or hydrogen, $R^3$ is a divalent alkylene radical which has having 1 to 12 carbon atoms and which may optionally be substituted by $C_1$ to $C_4$ alkyl groups and/or interrupted by one or more oxygen atoms, $R^4$ is a divalent organic radical which is formed by abstraction of both isocyanate groups from a cycloaliphatic or asymmetric aliphatic diisocyanate, and n and m independently of one another are positive numbers from 1 to 5.

In a second embodiment, the process of the first embodiment is modified, wherein $R^1$ is selected from the group consisting of 1,2-ethylene, 1,2- or 1,3-propylene, 1,2-, 1,3-, or 1,4-butylene, 1,1-dimethyl-1,2-ethylene, 1,2-dimethyl-1, 2-ethylene, 1,5-pentylene, 1,6-hexylene, 1,8-octylene, 1,10-decylene, and 1,12-dodecylene.

In a third embodiment, the process of the first and second embodiments is modified, wherein $R^3$ is selected from the group consisting of methylene, 1,2-ethylene, 1,2-propylene, 1,3-propylene, 1,2-butylene, 1,3-butylene, 1,4-butylene, 1,5-pentylene, 1,5-hexylene, 1,6-hexylene, 1,8-octylene, 1,10-decylene, 1,12-dodecylene, 2-oxa-1,4-butylene, 3-oxa-1,5-pentylene, and 3-oxa-1,5-hexylene.

In a fourth embodiment, the process of the first through third embodiments is modified, wherein (A) is selected from the group consisting of 2-hydroxyethyl(meth)acrylate, 2- or 3-hydroxypropyl(meth)acrylate, 1,4-butanediol mono(meth)acrylate, neopentyl glycol mono(meth)acrylate, 1,5-pentanediol mono(meth)acrylate, and 1,6-hexanediol mono(meth)acrylate.

In a fifth embodiment, the process of the first through fourth embodiments is modified, wherein (B) is selected from the group consisting of beta-propiolactone, gamma-butyrolactone, gamma-ethyl-gamma-butyrolactone, gamma-valerolactone, delta-valerolactone, epsilon-caprolactone, 7 methyloxepan-2-one, 1,4-dioxepan-5-one, oxacyclotridecan-2-one, and 13-butyl-oxacyclotridecan-2-one.

In a sixth embodiment, the process of the first through fifth embodiments is modified, wherein the bismuth compound (C) is a compound of bismuth in the +3 oxidation state with an anion selected from the group consisting of F—, Cl—, ClO—, $ClO_3$—, $ClO_4$—, Br—, I—, $IO_3$—, CN—, OCN—, $NO_2$—, $NO_3$—, $HCO_3$—, $CO_3^{2-}$, $S^{2-}$, SH—, $HSO_3$—, $SO_3^{2-}$, $HSO_4$—, $SO_4^{2-}$, $S_2O_2^{2-}$, $S_2O_4^{2-}$, $S_2O_5^{2-}$, $S_2O_6^{2-}$, $S_2O_7^{2-}$, $S_2O_8^{2-}$, $H_2PO_2$—, $H_2PO_4$—, $HPO_4^{2-}$, $PO_4^{3-}$, $P_2O_7^{4-}$, $(OC_xH_{2x+1})$—, $(C_xH_{2x-1}O_2)$—, $(C_xH_{2x-3}O_2)$—, and $(C_{x+1}H_{2x-2}O_4)^{2-}$, wherein x is a number 1 to 20.

In a seventh embodiment, the process of the first through fifth embodiments is modified, wherein the bismuth compound (C) is a bismuth carboxylate.

In an eighth embodiment, the process of the first through fifth embodiments is modified, wherein the bismuth compound (C) is selected from the group consisting of bismuth formate, acetate, propionate, hexanoate, neodecanoate, 2-ethylhexanoate, octoates, or pivalate.

In a ninth embodiment, the process of the first through fifth embodiments is modified, wherein the zinc compound (C) is a compound of zinc in the +2 oxidation state with an anion selected from the group consisting of F—, Cl—, ClO—, $ClO_3$—, $ClO_4$—, Br—, I—, $IO_3$—, CN—, OCN—, $NO_2$—, $NO_3$—, $HCO_3$—, $CO_3^{2-}$, $S_2$—, SH—, $HSO_3$—, $SO_3^{2-}$, $HSO_4$—, $SO_4^{2-}$, $S_2O_2^{2-}$, $S_2O_4^{2-}$, $S_2O_5^{2-}$, $S_2O_6^{2-}$, $S_2O_7^{2-}$, $S_2O_8^{2-}$, $H_2PO_2$—, $H_2PO_4$—, $HPO_4^{2-}$, $PO_4^{3-}$, $P_2O_7^{4-}$, $(OC_xH_{2x+1})$—, $(C_xH_{2x-1}O_2)$—, $(C_xH_{2x-3}O_2)$—, and $(C_{x+1}H_{2x-2}O_4)^{2-}$, wherein x is a number 1 to 20.

In a tenth embodiment, the process of the first through ninth embodiments is modified, wherein the first step is carried out at a temperature from 50 to 150° C. over a period from 3 to 48 hours.

In an eleventh embodiment, the process of the first through tenth embodiments is modified, wherein components (A) and (B) in the first step are present in a stoichiometric ratio of 1:1.5 to 3.

In a twelfth embodiment, the process of the first through eleventh embodiments is modified, wherein the catalyst (C) is added to the reaction mixture in an amount from 0.001 to 2 wt %, based on the sum of components (A) and (B).

In a thirteenth embodiment, the process of the first through twelfth embodiments is modified, wherein the second step is carried out at 40 to 100° C.

In a fourteenth embodiment, the process of the first through thirteenth embodiments is modified, wherein the bismuth-containing product of the first step contains hydroxyl groups, and wherein the second step is carried out at a stoichiometry from 1.2:1 to 1:1.2 of hydroxyl groups in the bismuth-containing product to isocyanate groups in component (D).

A second aspect of the present invention is directed to the use of urethane(meth)acrylates obtained the process of the first through fourteenth embodiments in radiation-curable coating materials.

A third aspect of the present invention is directed to urethane (meth)acrylates. A sixteenth embodiment is directed a urethane (meth)acrylate prepared by the process of the first through fourteenth embodiments.

A fourth aspect of the present invention is directed to a radiation-curable coating material. In a seventeenth embodiment, a radiation-curable coating material comprises the urethane (meth)acrylate of the sixteenth embodiment.

DETAILED DESCRIPTION

Described is a reaction regime for preparing urethane (meth)acrylates in which the addition product of lactone and hydroxyalkyl (meth)acrylate is obtained in a more uniform form than in the prior art, in order to obtain increased flexibility for applications on flexible substrates, for example. The aim here is to use a catalyst which can also be used in the subsequent step for preparing the urethane.

Specifically, described is a process for preparing urethane (meth)acrylates of the formula (I)

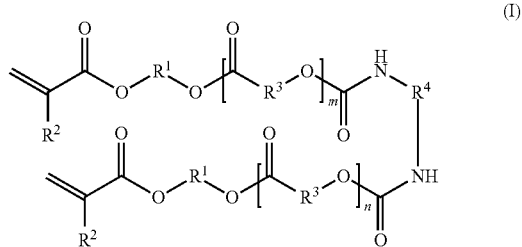

(I)

by in a first step reacting a hydroxyalkyl (meth)acrylate (A) of the formula (A)

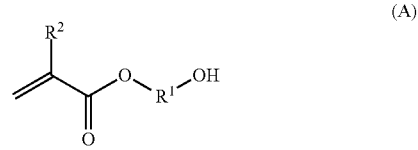

(A)

with a lactone (B) of the formula (B)

(B)

in the presence of at least one zinc compound and/or bismuth compound (C), and in a further step reacting the resulting zinc-containing and/or bismuth-containing product from the first step with at least one cycloaliphatic or asymmetric aliphatic diisocyanate (D).

In the formula above, $R^1$ is a divalent alkylene radical which has 2 to 12 carbon atoms and which may optionally be substituted by $C_1$ to $C_4$ alkyl groups and/or interrupted by one or more oxygen atoms, said radical specifically having 2 to 10 carbon atoms, more specifically 2 to 8, and very specifically having 3 to 6 carbon atoms, $R^2$ in each case independently of any other is methyl or hydrogen, specifically hydrogen, $R^3$ is a divalent alkylene radical which has 1 to 12 carbon atoms and which may optionally be substituted by $C_1$ to $C_4$ alkyl groups and/or interrupted by one or more oxygen atoms, said radical having specifically 2 to 10, more specifically 3 to 8, and very specifically 3 to 4 carbon atoms, and n and m independently of one another are positive numbers from 1 to 5, specifically 2 to 5, more specifically 2 to 4, very specifically 2 to 3, and more particularly 2 to 2.5.

$R^4$ here is a divalent organic radical which is formed by abstraction of both isocyanate groups from a cycloaliphatic or asymmetric aliphatic diisocyanate. Examples of such cycloaliphatic or asymmetric aliphatic diisocyanates are given below.

The values for n and m may on average also adopt uneven values, but in that case are of course even relative to each individual molecule of the formula above.

For the purposes of this specification, $C_1$-$C_4$ alkyl is methyl, ethyl, n-propyl, isopropyl, n-butyl, isobutyl, sec-butyl, or tert-butyl, specifically methyl, ethyl, and n-butyl, and more specifically methyl.

Examples of the radical $R^1$ are 1,2-ethylene, 1,2- or 1,3-propylene, 1,2-, 1,3-, or 1,4-butylene, 1,1-dimethyl-1,2-ethylene, 1,2-dimethyl-1,2-ethylene, 1,5-pentylene, 1,6-hexylene, 1,8-octylene, 1,10-decylene, or 1,12-dodecylene. Preference is given to 1,2-ethylene, 1,2- or 1,3-propylene, 1,4-butylene, and 1,6-hexylene, particular preference to 1,2-ethylene, 1,2-propylene, and 1,4-butylene, and special preference to 1,2-ethylene.

Examples of the radical $R^3$ are methylene, 1,2-ethylene, 1,2-propylene, 1,3-propylene, 1,2-butylene, 1,3-butylene, 1,4-butylene, 1,5-pentylene, 1,5-hexylene, 1,6-hexylene, 1,8-octylene, 1,10-decylene, 1,12-dodecylene, 2-oxa-1,4-butylene, 3-oxa-1,5-pentylene, or 3-oxa-1,5-hexylene, specifically 1,3-propylene, 1,4-butylene, 1,5-pentylene, 1,5-hexylene, and 1,12-dodecylene, more specifically 1,5-pentylene.

In one or more embodiments, the urethane (meth)acrylates of the present invention are those of the formula

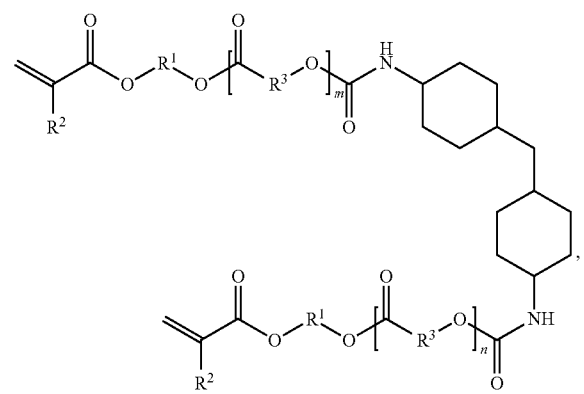

in which $R^1$ to $R^3$ have the definitions above.

In accordance with the present invention the first step is that of reacting hydroxyalkyl(meth)acrylates (A) of the formula

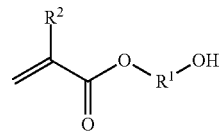

in which $R^1$ and $R^2$ have the definitions set out above with (n+m)/2 equivalents of lactone (B) of the formula

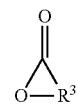

in which $R^3$ has the definitions set out above, to give an intermediate of the formula

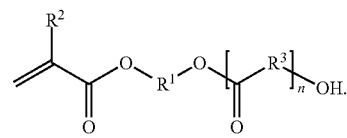

In one or more embodiments, the hydroxyalkyl(meth)acrylates (A) are selected from 2-hydroxyethyl(meth)acrylate, 2- or 3-hydroxypropyl(meth)acrylate, 1,4-butanediol mono(meth)acrylate, neopentyl glycol mono(meth)acrylate, 1,5-pentanediol mono(meth)acrylate, and 1,6-hexanediol mono(meth)acrylate, very specifically 2-hydroxyethyl (meth)acrylate, 2-hydroxypropyl(meth)acrylate, and 1,4-butanediol mono(meth)acrylate, and especially 2-hydroxyethyl (meth)acrylate.

In one or more embodiments, the acrylates here are used in each case over the methacrylates.

The lactone (B) has the following formula:

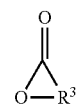

In one or more embodiments, the lactones are selected from beta-propiolactone, gamma-butyrolactone, gamma-ethyl-gamma-butyrolactone, gamma-valerolactone, delta-valerolactone, epsilon-caprolactone, 7-methyloxepan-2-one, 1,4-dioxepan-5-one, oxacyclotridecan-2-one, and 13-butyl-oxacyclotridecan-2-one.

In one or more specific embodiments, the lactones are selected from gamma-butyrolactone, delta-valerolactone, and epsilon-caprolactone; especially epsilon-caprolactone.

In accordance with the invention the reaction takes place in the first step in the presence of at least one zinc compound and/or bismuth compound (C), as for example one to three, specifically one or two, and very specifically just one zinc compound or bismuth compound. In one or more embodiments, the zinc compounds are used over the bismuth compounds.

In one or more embodiments, the compounds of bismuth are those in the +3 oxidation state; specifically zinc compounds in the +2 oxidation state.

Zinc compounds (C) contemplated include more specifically compounds of zinc in the +2 oxidation state, with the following anions: F—, Cl—, ClO—, $ClO_3$—, $ClO_4$—, Br—, I—, $IO_3$—, CN—, OCN—, $NO_2$—, $NO_3$—, $HCO_3$—, $CO_3^{2-}$, $S^{2-}$, SH—, $HSO_3$—, $SO_3^{2-}$, $HSO_4$—, $SO_4^{2-}$, $S_2O_2^{2-}$, $S_2O_4^{2-}$, $S_2O_5^{2-}$, $S_2O_6^{2-}$, $S_2O_7^{2-}$, $S_2O_5^{2-}$, $H_2PO_2$—, $H_2PO_4$—, $HPO_4^{2-}$, $PO_4^{3-}$, $P_2O_7^{4-}$, $(OC_xH_{2x+1})$—, $(C_xH_{2x-1}O_2)$—, $(C_xH_{2x-3}O_2)$—, and $(C_{x+1}H_{2x-2}O_4)^{2-}$, where x stands for the numbers 1 to 20. Preference here is given to the carboxylates in which the anion conforms to the formulae $(C_xH_{2x-1}O_2)$— and also $(C_{x+1}H_{2x-2}O_4)^{2-}$, with n being 1 to 20. In one or more embodiments, the salts have monocarboxylate anions of the general formula $(C_xH_{2x-1}O_2)$—, where x stands for the numbers 1 to 20, specifically 1 to 10. Particularly noteworthy among these are formate, acetate, propionate, hexanoate, neodecanoate, and 2-ethylhexanoate.

In one or more embodiments the zinc carboxylates are used as the zinc catalysts, more specifically those carboxylates which have at least six carbon atoms, more particularly zinc octoates, 2-ethylhexanoates, neodecanoates, or pivalates; an example is Borchi® Kat 22 from OMG Borchers GmbH, Langenfeld, Germany.

Bismuth compounds (C) contemplated include specifically compounds of bismuth in the +3 oxidation state, with the following anions: F—, Cl—, ClO—, $ClO_3$—, $ClO_4$—, Br—, I—, $IO_3$—, CN—, OCN—, $NO_2$—, $NO_3$—, $HCO_3$—, $CO_3^{2-}$, $S^{2-}$, SH—, $HSO_3$—, $SO_3^{2-}$, $HSO_4$—, $SO_4^{2-}$, $S_2O_2^{2-}$, $S_2O_4^{2-}$, $S_2O_5^{2-}$, $S_2O_6^{2-}$, $S_2O_7^{2-}$, $S_2O_8^{2-}$, $H_2PO_2$—, $H_2PO_4$—, $HPO_4^{2-}$, $PO_4^{3-}$, $P_2O_7^{4-}$, $(OC_xH_{2x+1})$—, $(C_xH_{2x-1}O_2)$—, $(C_xH_{2x-3}O_2)$—, and $(C_{x+1}H_{2x-2}O_4)^{2-}$, where x stands for the numbers 1 to 20. Preference here is given to the carboxylates in which the anion conforms to the formulae $(C_xH_{2x-1}O_2)$— and also $(C_{x+1}H_{2x-2}O_4)^{2-}$ with n being 1 to 20. In one or more embodiments, the salts have monocarboxylate anions of the general formula $(C_xH_{2x-1}O_2)$— where x stands for the numbers 1 to 20, specifically 1 to 10. Particularly noteworthy among these are formate, acetate, propionate, hexanoate, neodecanoate, and 2-ethylhexanoate.

In one or more embodiments, the bismuth carboxylates are used as the bismuth catalysts, more specifically carboxylates which have at least six carbon atoms, more particularly bismuth octoates, ethylhexanoates, neodecanoates, or pivalates; examples are K-KAT 348, XC-B221; XC-C227, XC 8203, and XK-601 from King Industries, TIB KAT 716, 716LA, 716XLA, 718, 720, and 789 from TIB Chemicals, and those from Shepherd Lausanne, and also, for example Borchi® Kat 24; 315, and 320 from OMG Borchers GmbH, Langenfeld, Germany.

Mixtures of different metals may also be involved, as for example in Borchi® Kat 0245 from OMG Borchers GmbH, Langenfeld, Germany.

In one or more embodiments, the bismuth carboxylates selected from bismuth neodecanoate, zinc neodecanoate, zinc 2-ethylhexanoate, and bismuth 2-ethylhexanoate.

It is possible to boost further the activity of the catalysts through the presence of acids, as for example through acids having a pKa of <2.5, as described in EP 2316867 A1, or having a pKa of between 2.8 and 4.5, as described in WO 04/029121 A1. Preference is given to the use of acids having a pKa of not more than 4.8, more specifically of not more than 2.5.

The reaction of components (A) and (B) takes place specifically at temperatures from 50 to 150° C., specifically 70 to 130° C., over a period from 3 to 48 hours, specifically from 5 to 36 hours, with stirring or pumped circulation.

The components (A) and (B) are mixed with one another in the desired stoichiometry (mol:mol), which is specifically 1:1.5 to 3, more specifically 1:1.8 to 2.5, very specifically 1:2 to 2.3, and more particularly 1:2, and heated. It is also possible for component (A) to be introduced to start with and for (B) to be added only during or after heating.

Before, during, or after heating, the catalyst (C), optionally divided into two or more portions, is added to the mixture.

It is also possible first to react component (A) with only part of the compound (B), and to add the remainder of the compound (B) to the reaction at a later point in time.

In one or more embodiments, all three components, (A), (B), and (C), are mixed with one another and jointly heated and reacted.

The catalyst (C) is added to the reaction mixture generally in amounts from 0.001 to 2 wt %, based on the sum of components (A) and (B), specifically 0.005 to 1.5 wt %, more specifically 0.01 to 1, and very specifically 0.01 to 0.5 wt %.

It is optionally possible, although less desired, for the reaction to be carried out in the presence of at least one solvent.

Examples of such solvents are aromatic (including alkylated benzenes and naphthalenes) and/or (cyclo)aliphatic hydrocarbons and mixtures thereof, chlorinated hydrocarbons, ketones, esters, alkoxylated alkanoic acid alkyl esters, ethers, or mixtures of the solvents.

In one or more embodiments, aromatic hydrocarbon mixtures are those which comprise primarily aromatic C7 to C14 hydrocarbons and which may span a boiling range from 110 to 300° C., particular preference being given to toluene, o-, m-, or p-xylene, trimethylbenzene isomers, tetramethylbenzene isomers, ethylbenzene, cumene, tetrahydronaphthalene, and mixtures comprising them.

Examples thereof are the Solvesso® products from ExxonMobil Chemical, particularly Solvesso® 100 (CAS No. 64742-95-6, primarily C9 and C10 aromatics, boiling range about 154-178° C.), 150 (boiling range about 182-207° C.), and 200 (CAS No. 64742-94-5), and also the Shellsol® products from Shell, Caromax® (e.g., Caromax® 18) from Petrochem Carless, and Hydrosol from DHC (e.g., as Hydrosol® A 170). Hydrocarbon mixtures composed of paraffins, cycloparaffins, and aromatics are also available commercially under the designations Kristalloel (for example, Kristalloel 30, boiling range about 158-198° C., or Kristallöl 60: CAS No. 64742-82-1), white spirit (for example, likewise CAS No. 64742-82-1), or solvent naphtha (light: boiling range about 155-180° C., heavy: boiling range about 225-300° C.). The aromatics content of such hydrocarbon mixtures is generally more than 90 wt %, specifically more than 95, more specifically more than 98, and very specifically more than 99 wt %. It may be advisable to use hydrocarbon mixtures having a particularly reduced naphthalene content.

(Cyclo)aliphatic hydrocarbons are, for example, decalin, alkylated decalin, and isomer mixtures of linear or branched alkanes and/or cycloalkanes.

The aliphatic hydrocarbon content is generally less than 5, specifically less than 2.5, and more specifically less than 1 wt %.

Esters are, for example, n-butyl acetate, ethyl acetate, 1-methoxyprop-2-yl acetate, and 2-methoxyethyl acetate.

Ethers are, for example, THF, dioxane, and the dimethyl, diethyl, or di-n-butyl ethers of ethylene glycol, diethylene glycol, triethylene glycol, propylene glycol, dipropylene glycol, or tripropylene glycol.

Ketones are, for example, acetone, diethyl ketone, ethyl methyl ketone, isobutyl methyl ketone, methyl amyl ketone, and tert-butyl methyl ketone.

In one or more embodiments, solvents are n-butyl acetate, ethyl acetate, 1-methoxyprop-2-yl acetate, 2-methoxyethyl acetate, and also mixtures thereof, especially with the aromatic hydrocarbon mixtures recited above, more particularly xylene and Solvesso® 100.

Such mixtures may be made in a volume ratio of 5:1 to 1:5, specifically in a volume ratio of 4:1 to 1:4, more specifically in a volume ratio of 3:1 to 1:3, and very specifically in a volume ratio of 2:1 to 1:2.

In one or more embodiments, examples are butyl acetate/xylene, 1:1 methoxypropyl acetate/xylene, 1:1 butyl acetate/solvent naphtha 100, 1:2 butyl acetate/Solvesso® 100, and 3:1 Kristalloel 30/Shellsol® A.

Preference is given to butyl acetate, 1-methoxyprop-2-yl acetate, methyl amyl ketone, xylene, and Solvesso® 100.

In general it is necessary and preferable for the reaction to be carried out in the presence of at least one stabilizer to counter radical polymerization of component (A), this stabilizer being specifically hydroquinone monomethyl ether and/or phenothiazine. It is also possible, though, for other stabilizers known for the stabilization of (meth)acrylates with respect to radical polymerization to be used.

The first reaction step is at an end when the lactone (B) has undergone substantial reaction, specifically to an extent of at least 90%, more specifically at least 95, very specifically at least 97, and more particularly at least 98%.

It is possible for unreacted lactone (B) and solvent optionally used to be removed from the reaction mixture, specifically by distillation, though in a specific embodiment the reaction mixture obtained from the first step is used directly in the second step, the reaction with component (D).

It is possible to terminate the reaction from the first step specifically by cooling. In this form the reaction mixture can be stored and can then be used at a later point in time, in the second step.

In the second reaction step, the reaction mixture obtained from the first step is then reacted with component (D).

Component (D) is at least one, specifically precisely one, cycloaliphatic or asymmetric aliphatic diisocyanate.

Cycloaliphatic diisocyanates are those diisocyanates in which at least one isocyanate group is bonded to a cyclic, nonaromatic ring system.

Aliphatic diisocyanates are those in which both isocyanate groups are each bonded to an $sp^3$-hybridized carbon atom that is not part of a ring system.

Asymmetric aliphatic diisocyanates are those aliphatic diisocyanates in which the isocyanate groups are connected by a divalent organic radical which has no plane of symmetry perpendicular to the axis to which the two isocyanate groups are joined.

In one or more embodiments, cycloaliphatic diisocyanates are 1,4-, 1,3-, or 1,2-diisocyanatocyclohexane, 4,4'- or 2,4'-di(isocyanatocyclohexyl)methane, bis(isocyanatomethyl)bicyclo[2.2.1]heptane (NBDI), 1-isocyanato-3,3,5-trimethyl-5-(isocyanatomethyl)cyclohexane(isophorone diisocyanate), 1,3- or 1,4-bis(isocyanatomethyl)cyclohexane or 2,4- or 2,6-diisocyanato-1-methylcyclohexane, and also 3(or 4),8(or 9)-bis(isocyanatomethyl)tricyclo[5.2.1.0$^{2.6}$]decane isomer mixtures.

In one or more embodiments, asymmetric aliphatic diisocyanates are derivatives of lysine diisocyanate, or tetramethylxylylene diisocyanate, trimethylhexane diisocyanate, or tetramethylhexane diisocyanate.

In one or more embodiments, the compounds (D) are selected from isophorone diisocyanate, 4,4'-di(isocyanatocyclo-hexyl)methane, and 2,2,4- and 2,4,4-trimethylhexane diisocyanate; very particular preference is given to di(isocyanatocyclohexyl)methane, 2,2,4- and 2,4,4-trimethylhexane diisocyanate, and especially 4,4'-di(isocyanatocyclohexyl)methane.

Dicyclohexylmethane 4,4'-diisocyanate may be present in the form of a mixture of the various cis and trans isomers, and may also include a fraction of 2,4'-di(isocyanatocyclohexyl)methane.

For the present invention it is possible to use not only those diisocyanates obtained by phosgenating the corresponding amines but also those diisocyanates prepared without the use of phosgene, i.e., by phosgene-free methods. Diisocyanates obtained accordingly generally have a very low fraction or even an unmeasurable fraction of chlorinated compounds, and this represents an advantage, for example, for applications in the electronics industry.

In one embodiment of the present invention, the isocyanates used have a hydrolyzable chlorine content of less than 100 ppm, specifically less than 50 ppm, more particularly less than 30 ppm, and especially less than 20 ppm. This can be measured, for example, using ASTM specification D4663-98. The total chlorine contents are, for example, below 1000 ppm, specifically below 800 ppm, and more specifically below 500 ppm (determined by argentometric titration after hydrolysis).

The second reaction step is carried out in a stoichiometry of 1.2:1 to 1:1.2 in terms of hydroxyl groups in the reaction product from the first step to isocyanate groups in component (D), specifically 1.1:1 to 1:1.1, more specifically 1.05:1 to 1:1.05, and very specifically 1:1.

The reaction in the second step takes place specifically at 40 to 100° C., more specifically 50 to 90, very specifically at 60 to 80° C.

For this step, the reaction mixture obtained from the first reaction step is brought to the desired temperature and component (D) is introduced in two or more portions or, specifically, in one portion.

Generally and with preference, the catalyst (C), present in the reaction mixture from the reaction in the first step, is sufficient to catalyze the reaction between isocyanate groups and hydroxyl groups as well. Should this not be the case, then further catalyst (C) may be metered in subsequently.

The reaction is continued until the NCO value has dropped to below 1 wt %, specifically below 0.5 wt %, more specifically below 0.3, very specifically below 0.2, and more particularly below 0.1 wt %.

If the reaction has been carried out in the presence of a solvent, this solvent can now be separated off, specifically by distillation.

It is possible, although generally not necessary, for the catalyst to be removed from the resulting reaction mixture.

Its removal may take place, for example, by washing or filtration.

For this purpose the reaction mixture is neutralized in a washing apparatus with a 5-25, specifically 5-20, more specifically 5-15 wt % strength aqueous solution of a base, such as sodium hydroxide, potassium hydroxide, sodium hydrogencarbonate, sodium carbonate, potassium hydrogencarbonate, calcium hydroxide, aqueous ammonia, or potassium carbonate, for example, which may optionally have been admixed with 5-15 wt % of sodium chloride, potassium chloride, ammonium chloride, or ammonium sulfate, neutralization taking place specifically with aqueous sodium hydroxide solution or aqueous sodium hydroxide/sodium chloride solution.

Washing may be carried out, for example, in a stirred tank or in other conventional apparatus, such as in a column or mixer-settler apparatus, for example.

The organic phase from the initial wash is then treated with water or with a 5-30 wt %, specifically 5-20, more specifically 5-15 wt % strength solution of sodium chloride, potassium chloride, ammonium chloride, sodium sulfate, or ammonium sulfate, specifically sodium chloride solution.

It is also possible, however, for traces of catalyst to be removed from the reaction mixture by filtering it over activated carbon, aluminum oxide, silica, or ion exchangers.

The product obtained in accordance with the method of the invention can be used in a conventional way in radiation-curable coating materials and has the advantage that in the product of the first stage, the distribution of the lactone units (B) is more uniform than in accordance with the processes from the prior art. A consequence of this is that the coating materials which comprise a product obtained by the process of the invention exhibit a high flexibility.

Likewise provided by the present invention, accordingly, is the use of urethane(meth)acrylates obtained by the process of the invention in radiation-curable coating materials.

The coating materials of these kinds are suitable for coating substrates such as wood, paper, textile, leather, nonwoven, plastics surfaces, PVC, glass, ceramic, mineral building materials, such as shaped cement blocks and fiber-cement slabs, or coated or uncoated metals, specifically plastics or metals, more particularly in the form of films or foils, very specifically metals.

The coating agents may be used more particularly in primers, primer-surfacers, pigmented top-coat materials, and clearcoat materials in the automotive refinish or large-vehicle finishing and aircraft sectors. Coating agents of this kind are particularly suitable for applications requiring particularly high application reliability, external weathering resistance, hardness, and flexibility, such as in automotive refinish and large-vehicle finishing.

The examples given below are intended to elucidate the present invention, but without restricting it.

The % and ppm figures stated in this specification relate to wt % and wt-ppm, unless otherwise indicated.

EXAMPLES

Inventive Example 1

323 parts of epsilon-caprolactone, 164 parts of hydroxyethyl acrylate, and 0.5 part of bismuth 2-ethylhexanoate (BorchiKat® 24 from OMG Borchers GmbH, Langenfeld, Germany) were heated at 105-110° C. for 35 hours, followed by cooling to 60° C. and addition of 187 parts of a diisocyanate based on H12-MDI (Desmodur® W from Bayer MaterialScience), and by reaction for a further 14 hours at 80-85° C. The isocyanate value had dropped to <0.1%. This gave a viscous, clear urethane acrylate having a viscosity of 27.5 Pas (measured using an Epprecht cone/plate viscometer (cone C) at 23° C. The GPC chromatograms for the first and second stages show somewhat less low molecular mass products than those of comparative example 1, in which the first stage was prepared using an organotin catalyst.

Inventive Example 2

323 parts of epsilon-caprolactone, 164 parts of hydroxyethyl acrylate, and 0.1 part of zinc 2-ethylhexanoate (Bor-chiKat® 22 from OMG Borchers GmbH, Langenfeld, Germany) were heated at 105-110° C. for 11 hours, followed by cooling to 60° C. and addition of 187 parts of a diisocyanate based on H12-MDI (Desmodur® W from Bayer MaterialScience), and by reaction for a further 14 hours at 80-85° C. The isocyanate value had dropped to <0.1%. This gave a viscous, clear urethane acrylate having a viscosity of 24.0 Pas (measured using an Epprecht cone/plate viscometer (Cone C) at 23° C. The GPC chromatograms for the first and second stages correspond to those of inventive example 1.

Comparative Example 1

323 parts of epsilon-caprolactone, 164 parts of hydroxyethyl acrylate, and 0.05 part of butyltin tris(2-ethylhexanoate) were heated at 105-110° C. for 11 hours, followed by cooling to 60° C. and addition of 187 parts of a diisocyanate based on H12-MDI (Desmodur® W from Bayer MaterialScience), and by reaction for a further 14 hours at 80-85° C. The isocyanate value had dropped to <0.1%. This gave a viscous, clear urethane acrylate having a viscosity of 19.8 Pas (measured using an Epprecht cone/plate viscometer (Cone C).

Comparative Examples of the First Stage 323 parts of epsilon-caprolactone, 164 parts of hydroxyethyl acrylate, and x parts of catalyst, as indicated in the table, were heated for y hours, as indicated in the table, at 105-110° C. The viscosity of the resulting reaction mixture was then ascertained at 23° C.

| Catalyst | Catalyst amount/reaction time | Viscosity (mPas) |
|---|---|---|
| Butyltin trisethylhexanoate | 0.01/11 | 85 |
| Bismuth ethylhexanoate (inventive) | 0.2/35 | 95 |
| Tetrabutyl orthotitanate | 0.1/11 | 55 |
| Phosphoric acid | 0.05/11 | 100 |
| p-Toluenesulfonic acid | 0.1/11 | 125 |
| Zinc ethylhexanoate (inventive) | 0.1/11 | 80 |
| Cesium acetate | 0.1/11 | 5 |

The GPC data (measured by gel permeation chromatography with tetrahydrofuran and polystyrene as standard) for the first stage with the following catalysts are as follows:

| | |
|---|---|
| p-Toluenesulfonic acid | Mn = 546 g/mol |
| Butyltin trisethylhexanoate | Mn = 460 g/mol |
| Zinc ethylhexanoate | Mn = 455 g/mol |
| Tetrabutyl titanate | Mn = 401 g/mol |

From the viscosity and the number-average molar weight Mn it is evident that the Brönsted catalysts phosphoric acid and p-toluenesulfonic acid deliver a higher molecular mass product in comparison to the tin catalysis.

Catalysis with tetrabutyl orthotitanate or cesium acetate, in contrast, yields a product which does not achieve the molecular weight of the tin catalysis product.

In contrast, with the zinc and bismuth catalysis of the invention, viscosity and product spectrum match those of the comparative product.

Example 3

Determination of Flexibility 60 parts of each of the oligomers from inventive examples 1 and 2 and from the comparative example were blended with 40 parts of dipropylene glycol diacrylate, 4.5 parts of the photoinitiator benzophenone, and 4 parts of the photoinitiator Darocure® 1173, and this blend was applied in a film thickness of approximately 12 μm to a rigid polyvinyl chloride film. UV radiation exposure then took place on an IST belt unit with a speed of 10 m/min (about 1400 mJ/cm²).

The films coated with a varnish layer in this way were subjected to a mandrel bending test, by pulling the film around a mandrel with decreasing diameter and assessing whether the varnish layer displays cracks. The smaller the diameter of the mandrel, the greater the flexibility of the varnish layer must be.

| No. | 15 mm mandrel diameter | 10 mm mandrel diameter |
|---|---|---|
| Inventive example 1 | ok | ok |
| Inventive example 2 | ok | ok |
| Comparative example 1 | ok | cracks |

What is claimed is:

1. A process for preparing urethane (meth)acrylates of the formula (I)

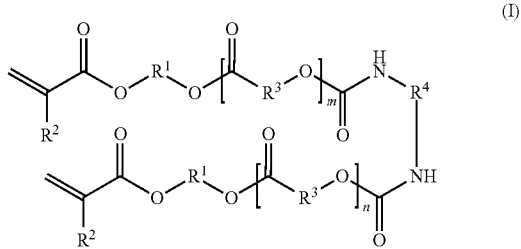

comprising, in a first step, reacting a hydroxyalkyl (meth) acrylate (A) of the formula (A)

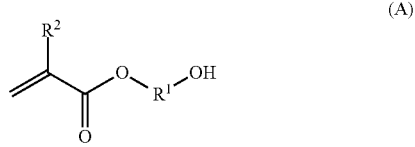

with a lactone of the formula (B)

in the presence of only one zinc compound or bismuth compound (C) and in the absence of an acid to produce a corresponding resulting zinc-containing product or a bismuth-containing product, and, in a further step, reacting the zinc-containing product or the bismuth-containing product with at least one cycloaliphatic or asymmetric aliphatic diisocyanate (D), wherein
$R^1$ is a divalent alkylene radical having 2 to 12 carbon atoms and which may optionally be substituted by C1 to C4 alkyl groups and/or interrupted by one or more oxygen atoms,
$R^2$ in each case independently of any other is methyl or hydrogen,
$R^3$ is a divalent alkylene radical having 1 to 12 carbon atoms and which may optionally be substituted by C1 to C4 alkyl groups and/or interrupted by one or more oxygen atoms,
$R^4$ is a divalent organic radical which is formed by abstraction of both isocyanate groups from a cycloaliphatic or asymmetric aliphatic diisocyanate, and
n and m independently of one another are positive numbers from 1 to 5.

2. The process of claim 1, wherein $R^1$ is selected from the group consisting of 1,2-ethylene, 1,2- or 1,3-propylene, 1,2-, 1,3-, or 1,4-butylene, 1,1-dimethyl-1,2-ethylene, 1,2-dimethyl-1,2-ethylene, 1,5-pentylene, 1,6-hexylene, 1,8-octylene, 1,10-decylene, and 1,12-dodecylene.

3. The process of claim 1, wherein $R^3$ is selected from the group consisting of methylene, 1,2-ethylene, 1,2-propylene, 1,3-propylene, 1,2-butylene, 1,3-butylene, 1,4-butylene, 1,5-pentylene, 1,5-hexylene, 1,6-hexylene, 1,8-octylene, 1,10-decylene, 1,12-dodecylene, 2-oxa-1,4-butylene, 3-oxa-1,5-pentylene, and 3-oxa-1,5-hexylene.

4. The process of claim 1, wherein (A) is selected from the group consisting of 2-hydroxyethyl (meth)acrylate, 2- or 3-hydroxypropyl (meth)acrylate, 1,4-butanediol mono (meth)acrylate, neopentyl glycol mono(meth)acrylate, 1,5-pentanediol mono(meth)acrylate, and 1,6-hexanediol mono (meth)acrylate.

5. The process of claim 1, wherein (B) is selected from the group consisting of beta-propiolactone, gamma-butyrolactone, gamma-ethyl-gamma-butyrolactone, gamma-valerolactone, delta-valerolactone, epsilon-caprolactone, 7-methyloxepan-2-one, 1,4-dioxepan-5-one, oxacyclotridecan-2-one, and 13-butyl-oxacyclotridecan-2-one.

6. The process of claim 1, wherein the bismuth compound (C) is present and is a compound of bismuth in the +3 oxidation state with an anion selected from the group consisting of F, Cr, Cl$^-$, ClO$_3^-$, ClO$_4^-$, Br$^-$, I$^-$, IO$_3^-$, CN$^-$, OCN$^-$, NO$_2^-$, NO$_3^-$, HCO$_3^-$, CO$_3^{2-}$, S$^{2-}$, SH$^-$, HSO$_3^-$, SO$_3^{2-}$, HSO$_4^-$, SO$_4^{2-}$, S$_2$O$_2^{2-}$, S$_2$O$_5^{2-}$, S$_2$O$_6^{2-}$, S$_2$O$_7^{2-}$, S$_2$O$_8^{2-}$, H$_2$PO$_2^-$, H$_2$PO$_4^-$, HPO$_4^{2-}$, PO$_4^{3-}$, P$_2$O$_7^{4-}$, (OC$_x$H$_{2x+1}$)$^-$, (C$_x$H$_{2x-1}$O$_2$)$^-$, (C$_x$H$_{2x-3}$ O$_2$)$^-$, and (C$_{x+1}$H$_{2x-2}$O$_2$)$^{2-}$, wherein x is a number 1 to 20.

7. The process of claim 1, wherein the bismuth compound (C) is present and is a bismuth carboxylate.

8. The process of claim 1, wherein the bismuth compound (C) is present and is selected from the group consisting of bismuth formate, acetate, propionate, hexanoate, neodecanoate, 2-ethylhexanoate, octoates, or pivalate.

9. The process of claim 1, wherein the zinc compound (C) is present and is a compound of zinc in the +2 oxidation state with an anion selected from the group consisting of F, Cr, Cl$^-$, ClO$_3^-$, ClO$_4^-$, Br$^-$, I$^-$, IO$_3^-$, CN$^-$, OCN$^-$, NO$_2^-$, NO$_3^-$, HCO$_3^-$, CO$_3^{2-}$, S$^{2-}$, SH$^-$, HSO$_3^-$, SO$_3^{2-}$, HSO$_4^-$, SO$_4^{2-}$, S$_2$O$_2^{2-}$, S$_2$O$_6^{2-}$, S$_2$O$_7^{2-}$, S$_2$O$_8^{2-}$, H$_2$PO$_2^-$, H$_2$PO$_4^-$, HPO$_4^{2-}$, PO$_4^{3-}$, P$_2$O$_7^{4-}$, (OC$_x$H$_{2x+1}$)$^-$, (C$_x$H$_{2x+1}$)$^-$, (C$_x$H$_{2x-1}$O$_2$)$^-$, (C$_x$H$_{2x-3}$O$_2$)$^-$, and H$_2$PO$_2^-$, H$_2$PO$_4^-$, HPO$_4^{2-}$, PO$_4^{3-}$, P$_2$O$_7^{4-}$, (OC$_x$H$_{2x+1}$)$^-$, (C$_x$H$_{2x-1}$O$_2$)$^-$, (C$_x$H$_{2x-3}$O$_2$)$^-$, and (C$_{x+1}$H$_{2x-2}$O$_2$)$^{2-}$, wherein x is a number 1 to 20.

10. The process of claim 1, wherein the first step is carried out at a temperatures from 50 to 150° C. over a period from 3 to 48 hours.

11. The process of claim 1, wherein components (A) and (B) in the first step are present in a stoichiometric ratio of 1:1.5 to 3.

12. The process of claim 1, wherein the catalyst (C) is added to the reaction mixture in an amount from 0.001 to 2 wt %, based on the sum of components (A) and (B).

13. The process of claim 1, wherein the second step is carried out at 40 to 100° C.

14. The process of claim 1, wherein the bismuth-containing product of the first step contains hydroxyl groups, and wherein the second step is carried out at a stoichiometry from 1.2:1 to 1:1.2 of hydroxyl groups in the bismuth-containing product to isocyanate groups in component (D).

15. A process for preparing urethane (meth)acrylates of the formula (I)

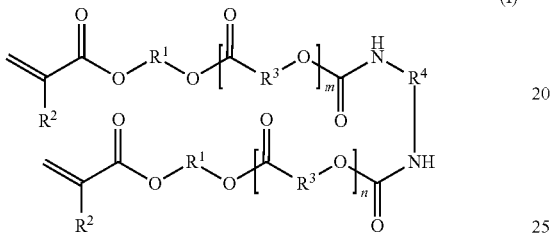

comprising, in a first step, reacting a hydroxyalkyl (meth)acrylate (A) of the formula (A)

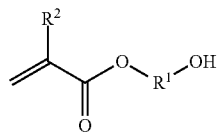

with a lactone of the formula (B)

in the presence of only one zinc compound (C) to produce a zinc-containing product, and, in a further step, reacting the zinc-containing product with at least one cycloaliphatic or asymmetric aliphatic diisocyanate (D), wherein $R^1$ is a divalent alkylene radical having 2 to 12 carbon atoms and which may optionally be substituted by C1 to C4 alkyl groups and/or interrupted by one or more oxygen atoms, $R^2$ in each case independently of any other is methyl or hydrogen, $R^3$ is a divalent alkylene radical having 1 to 12 carbon atoms and which may optionally be substituted by C1 to C4 alkyl groups and/or interrupted by one or more oxygen atoms, $R^4$ is a divalent organic radical which is formed by abstraction of both isocyanate groups from a cycloaliphatic or asymmetric aliphatic diisocyanate, and n and m independently of one another are positive numbers from 1 to 5.

16. The method of claim 15, wherein the zinc compound (C) is zinc ethyhexanoate.

* * * * *